(12) United States Patent
Han et al.

(10) Patent No.: US 11,085,034 B2
(45) Date of Patent: Aug. 10, 2021

(54) ENZYME COMPLEX COMPRISING HEME POLYMERASE AND HEME LIGASE, AND METHOD FOR PRODUCING HEMOZOIN USING SAME

(71) Applicant: KOREA UNIVERSITY RESEARCH AND BUSINESS FOUNDATION, Seoul (KR)

(72) Inventors: Sung Ok Han, Seoul (KR); Jeong-Eun Hyeon, Seoul (KR); Young-jin Ko, Chuncheon-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/466,390

(22) PCT Filed: Dec. 6, 2017

(86) PCT No.: PCT/KR2017/014181
§ 371 (c)(1),
(2) Date: May 26, 2020

(87) PCT Pub. No.: WO2018/106000
PCT Pub. Date: Jun. 14, 2018

(65) Prior Publication Data
US 2020/0291379 A1    Sep. 17, 2020

(30) Foreign Application Priority Data
Dec. 6, 2016    (KR) .................. 10-2016-0164899

(51) Int. Cl.
| | | |
|---|---|---|
| *C12N 9/22* | (2006.01) | |
| *C12N 9/96* | (2006.01) | |
| *C12N 9/10* | (2006.01) | |
| *C12N 9/88* | (2006.01) | |
| *C12P 17/18* | (2006.01) | |

(52) U.S. Cl.
CPC ............... *C12N 9/96* (2013.01); *C12N 9/10* (2013.01); *C12N 9/88* (2013.01); *C12P 17/182* (2013.01); *C12Y 499/01008* (2013.01)

(58) Field of Classification Search
None
See application file for complete search history.

(56) References Cited

U.S. PATENT DOCUMENTS 5,130,416 A  *  7/1992  Wellems .............. C07K 14/445
                                                     530/350
5,296,382 A  *  3/1994  Wellems .............. C07K 14/445
                                                     436/501
5,476,785 A  * 12/1995  Wellems .............. C07K 14/445
                                                     435/252.3
7,438,915 B2 * 10/2008  Lillehoj .............. C07K 14/375
                                                     424/191.1

FOREIGN PATENT DOCUMENTS

KR    10-2016-0040088 A    4/2016

OTHER PUBLICATIONS

Park, Jae-Seon, et al., "Cohesin-Dockerin Interactions of Cellulosomal Subunits of Clostridium cellulovorans", *Journal of bacteriology*, vol. 183, Issue 18, Sep. 2001 (pp. 5431-5435).
Jani, Dewal, et al., "HDP—A Novel Heme Detoxification Protein from the Malaria Parasite", *PLoS pathogens*, vol. 4, No. 4, Apr. 25, 2008 (pp. 1-16).
Karl, Stephan et al., "Enhanced detection of gametocytes by magnetic deposition microscopy predicts higher potential for Plasmodium falciparum transmission", *Malaria journal*, vol. 7, No. 1, 2008 (pp. 1-9).
"Plasmodium falciparum 3D7 heme detoxification protein (HDP) MRNA, complete cds", NCBI, Genbank Acession No. XM_001348584.1, May 27, 2010 (2 pages in English).
"Plasmodium falciparum 3D7 histidine rick protein II(HRPII) mNRA, Complete cds", NCBI, Genbank Accession No. XM_002808697.1, May 27, 2010 (2 pages in English).
Rebelo, Maria, et al/. "Haemozoin detection in infected erythrycytes for Plasmodium falciparum malaria diagnosis—Prospects and limitations", *Acta Tropica*, vol. 123, No. 1, Mar. 2012 (pp. 58-61).
Chugh, Monika, et al. "Protein complex directs hemoglobin-to-hemozoin formation in Plasmodium falciparum." *Proceedings of the National Academy of Sciences*, vol. 110, No. 14, Apr. 2, 2013, (pp. 5392-5397).
Rebelo, Maria et al., "Light Depolarization Measurements in Malaria: a New Job for an Old Friend", *Cytometry Part A*, vol. 87, No. 5, 2015 (pp. 437-445).
Korean Office Action dated Feb. 13, 2018 in counterpart Korean Application No. 10-2016-0164899 (7 pages in Korean).
International Search Report dated Dec. 10, 2018 in counterpart International Patent Application No. PCT/KR2017/014181 (3 pages in English and 3 pages in Korean).

\* cited by examiner

*Primary Examiner* — Hope A Robinson
(74) *Attorney, Agent, or Firm* — NSIP Law (57) ABSTRACT

The present invention relates to an enzyme complex in which a heme polymerase and a heme ligase are linked to each other via the dockerin module of cellulase, and to a method for producing a hemozoin using the same. The enzyme complex according to the present invention can polymerize heme with higher efficiency than conventional enzymes, and thus can more efficiently produce hemozoin, a conductive biopolymer.

3 Claims, 4 Drawing Sheets
Specification includes a Sequence Listing.

SEQUENCE LISTING

<160> NUMBER OF SEQ ID NOS: 31

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
gcgcgaattc gaataattcc gcatttaata ataacttgt                          39

<210> SEQ ID NO 2
<211> LENGTH: 846
<212> TYPE: DNA
<213> ORGANISM: Artificial Sequence
<220> FEATURE:
<223> OTHER INFORMATION: primer

<400> SEQUENCE: 2
aataattccg catttaataa taacttgtgt agcaaaaatg caaaaggact taatttaaat     60
aagagattat tacacgaaac tcaagcacat gtagatgatg cccatcatgc tcatcatgta    120
gccgatgccc atcatgctca tcatgtagcc gatgcccatc atgctcatca tgtagccgat    180
gcccatcatg ctcatcatgc agccgatgcc catcatgctc atcatgcagc cgatgcccat    240
catgctcatc atgcagccga tgcccatcat gctcatcatg ctcaccatgc agccgatgcc    300
catcacgctc atcatgcagc cgatgcccat catgctcacc atgcagctga tgctcatcac    360
gctcatcatg cagccgatgc ccatcatgct caccatgcag ctgatgctca tcacgctcat    420
catgcatccg atgcccatca tgctcatcat gcagcctatg cccatcatgc tcatcatgca    480
tccgatgctc atcatgcagc tgatgctcac catgcagctt atgcccatca cgctcatcat    540
gcagcggatg ctcatcatgc agccgatgct caccatgcaa ccgatgctca tcatgcagcc    600
gatgctcatc atgcagccga tgctcaccat gcagccgatg ctcaccatgc aaccgatgct    660
catcacgctc accatgcagc cgatgctcac catgcaaccg atgctcatca cgctcaccat    720
gcagccgatg ctcatcatgc agccgcacac catgcaactg atgctcacca tgcagccgca    780
caccatgcaa ccgatgctca ccatgcagcc gcacaccacg aagccgccac acattgccta    840
cgccat                                                              846

<210> SEQ ID NO 3
<211> LENGTH: 846
<212> TYPE: DNA
<213> ORGANISM: Artificial Sequence
<220> FEATURE:
<223> OTHER INFORMATION: Histidine rich protein 2-Exon2

<400> SEQUENCE: 3

```
aataattccg catttaataa taacttgtgt agcaaaaatg caaaaggact taatttaaat    60
aagagattat tacacgaaac tcaagcacat gtagatgatg cccatcatgc tcatcatgta   120
gccgatgccc atcatgctca tcatgtagcc gatgcccatc atgctcatca tgtagccgat   180
gcccatcatg ctcatcatgc agccgatgcc catcatgctc atcatgcagc cgatgcccat   240
catgctcatc atgcagccga tgcccatcat gctcatcatg ctcaccatgc agccgatgcc   300
catcacgctc atcatgcagc cgatgcccat catgctcacc atgcagctga tgctcatcac   360
gctcatcatg cagccgatgc ccatcatgct caccatgcag ctgatgctca tcacgctcat   420
catgcatccg atgcccatca tgctcatcat gcagcctatg cccatcatgc tcatcatgca   480
tccgatgctc atcatgcagc tgatgctcac catgcagctt atgcccatca cgctcatcat   540
gcagcggatg ctcatcatgc agccgatgct caccatgcaa ccgatgctca tcatgcagcc   600
gatgctcatc atgcagccga tgctcaccat gcagccgatg ctcaccatgc aaccgatgct   660
catcacgctc accatgcagc cgatgctcac catgcaaccg atgctcatca cgctcaccat   720
gcagccgatg ctcatcatgc agccgcacac catgcaactg atgctcacca tgcagccgca   780
caccatgcaa ccgatgctca ccatgcagcc gcacaccacg aagccgccac acattgccta   840
cgccat                                                             846

<210> SEQ ID NO 4
<211> LENGTH: 48
<212> TYPE: DNA
<213> ORGANISM: Artificial Sequence
<220> FEATURE:
<223> OTHER INFORMATION: primer

<400> SEQUENCE: 4
gcgcgaattc gatgaaaaat agattttatt ataatttgat aattaaaa              48

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
agctgccaac tgtaggatga tttaacagat tagaa                            35

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
tcatcctaca gttggcagct cgttaatac                                   29

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
acattaacca cggttggtaa gatgaacca                                   29
```

```
<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
ttaccaaccg tggttaatgt acaatgaaaa aagg                                  34

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
gcgcaagctt aaaaatgatg ggcttatcta ctata                                 35

<210> SEQ ID NO 10
<211> LENGTH: 216
<212> TYPE: DNA
<213> ORGANISM: Artificial Sequence
<220> FEATURE:
<223> OTHER INFORMATION: Exon1 of heme ligase

<400> SEQUENCE: 10
atgaaaaata gattttatta taatttgata attaaaagat tatatacacg aagtggcggt      60
ttaagaaaac ctcaaaaggt aaccaacgac ccagaaagta aaatagaaa agtatattgg      120 tgttttgaac ataagcctgt aaaaaggaca attattaatt aatatattc acataacgaa      180 ctcaagatat tttctaatct gttaaatcat cctaca                               216

<210> SEQ ID NO 11
<211> LENGTH: 204
<212> TYPE: DNA
<213> ORGANISM: Artificial Sequence
<220> FEATURE:
<223> OTHER INFORMATION: Exon2 of heme ligase

<400> SEQUENCE: 11
gttggcagct cgttaataca tgaattatct ctcgatggcc cttatactgc attttttccc      60
tccaacgaag ccatgcaatt aataaatata gaaagtttca ataaattgta taacgatgaa     120
aataaattat cagaatttgt tttaaatcac gttacgaaag aatattggct gtatagagat     180
ttatatggtt catcttacca accg                                            204

<210> SEQ ID NO 12
<211> LENGTH: 195
<212> TYPE: DNA
<213> ORGANISM: Artificial Sequence
<220> FEATURE:
<223> OTHER INFORMATION: Exon3 of heme ligase

<400> SEQUENCE: 12
tggttaatgt acaatgaaaa aagggaagct ccagaaaaat taagaaattt attgaataat      60
gatttaatag taaaaattga gggggaattt aaacattgca atcattcgat atatttaaat     120
ggctcaaaaa ttataagacc aaatatgaag tgccacaatg gagttgtgca tatagtagat     180
aagcccatca ttttt                                                      195
```

```
<210> SEQ ID NO 13
<211> LENGTH: 48
<212> TYPE: DNA
<213> ORGANISM: Artificial Sequence
<220> FEATURE:
<223> OTHER INFORMATION: primer

<400> SEQUENCE: 13
gcgcgaattc gatgaaaaat agattttatt ataatttgat aattaaaa                48

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
gcgcaagctt aaaaatgatg ggcttatcta ctata                              35

<210> SEQ ID NO 15
<211> LENGTH: 49
<212> TYPE: DNA
<213> ORGANISM: Artificial Sequence
<220> FEATURE:
<223> OTHER INFORMATION: primer

<400> SEQUENCE: 15
gcgctctaga tttaagaagg agatatacat atgaataatt ccgcattta               49

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
cagcggatcc atggcgtagg caatgtgt                                      28

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
cctacgccat ggatccgctg gctcc                                         25

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
atatctgcag tcagtggtgg tggtggtggt gtaaaagcat tttttaag                49

<210> SEQ ID NO 19
<211> LENGTH: 49
<212> TYPE: DNA
<213> ORGANISM: Artificial Sequence
<220> FEATURE:
<223> OTHER INFORMATION: primer
```

<400> SEQUENCE: 19
gcgctctaga tttaagaagg agatatacat atgaaaaata gatttttatt          49

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
cagcggatcc aaaaatgatg ggcttatcta ctatat                          36

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
catcattttt ggatccgctg gctccg                                     26

<210> SEQ ID NO 22
<211> LENGTH: 49
<212> TYPE: DNA
<213> ORGANISM: Artificial Sequence
<220> FEATURE:
<223> OTHER INFORMATION: primer

<400> SEQUENCE: 22
atatctgcag tcagtggtgg tggtggtggt gtaaaagcat tttttaag            49

<210> SEQ ID NO 23
<211> LENGTH: 159
<212> TYPE: DNA
<213> ORGANISM: Artificial Sequence
<220> FEATURE:
<223> OTHER INFORMATION: dockerin domain

<400> SEQUENCE: 23
gatgttaaca aagatggaaa ggtaaatgct atcgattatg cagtgcttaa atcaattctt          60
ttaggtacaa atactaacgt tgatttatca gtatcagaca tgaataagga tggtaaagta        120
aatgctttgg atttagctgt tcttaaaaaa atgctttta                              159

<210> SEQ ID NO 24
<211> LENGTH: 49
<212> TYPE: DNA
<213> ORGANISM: Artificial Sequence
<220> FEATURE:
<223> OTHER INFORMATION: primer

<400> SEQUENCE: 24
gcgctctaga tttaagaagg agatatacat atgaataatt ccgcattta            49

<210> SEQ ID NO 25
<211> LENGTH: 49
<212> TYPE: DNA
<213> ORGANISM: Artificial Sequence
<220> FEATURE:
<223> OTHER INFORMATION: primer

<400> SEQUENCE: 25
atatctgcag tcagtggtgg tggtggtggt gtaaaagcat tttttaag            49

<210> SEQ ID NO 26
<211> LENGTH: 49
<212> TYPE: DNA
<213> ORGANISM: Artificial Sequence
<220> FEATURE:
<223> OTHER INFORMATION: primer

<400> SEQUENCE: 26
gcgctctaga tttaagaagg agatatacat atgaaaaata gattttatt           49

<210> SEQ ID NO 27
<211> LENGTH: 49
<212> TYPE: DNA
<213> ORGANISM: Artificial Sequence
<220> FEATURE:
<223> OTHER INFORMATION: primer

<400> SEQUENCE: 27
atatctgcag tcagtggtgg tggtggtggt gtaaaagcat tttttaag            49

<210> SEQ ID NO 28
<211> LENGTH: 615
<212> TYPE: DNA
<213> ORGANISM: Artificial Sequence
<220> FEATURE:
<223> OTHER INFORMATION: Conjugated sequence of Exon 1, Exon2 and Exon3

<400> SEQUENCE: 28
atgaaaaata gattttatta taatttgata attaaaagat tatatacacg aagtggcggt      60
ttaagaaaac ctcaaaaggt aaccaacgac ccagaaagta taaatagaaa agtatattgg     120
tgttttgaac ataagcctgt aaaaaggaca attattaatt taatatattc acataacgaa     180
ctcaagatat tttctaatct gttaaatcat cctacagttg gcagctcgtt aatacatgaa     240
ttatctctcg atggccctta tactgcattt tttccctcca acgaagccat gcaattaata     300
aatatagaaa gtttcaataa attgtataac gatgaaaata aattatcaga atttgtttta     360
aatcacgtta cgaaagaata ttggctgtat agagatttat atggttcatc ttaccaaccg     420
tggttaatgt acaatgaaaa aagggaagct ccagaaaaat taagaaattt attgaataat     480
gatttaatag taaaaattga gggggaattt aaacattgca atcattcgat atatttaaat     540
ggctcaaaaa ttataagacc aaatatgaag tgccacaatg gagttgtgca tatagtagat     600
aagcccatca ttttt                                                      615

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
ggatccgcag cgacatcatc aa                                               22

<210> SEQ ID NO 30
<211> LENGTH: 33
<212> TYPE: DNA
<213> ORGANISM: Artificial Sequence
<220> FEATURE:
<223> OTHER INFORMATION: primer

<400> SEQUENCE: 30

```
gcgcctcgag gctataggat ctccaatatt tat                                   33
```

<210> SEQ ID NO 31
<211> LENGTH: 1647
<212> TYPE: DNA
<213> ORGANISM: Artificial Sequence
<220> FEATURE:
<223> OTHER INFORMATION: mCbpA

<400> SEQUENCE: 31

```
gcagcgacat catcaatgtc agttgaattt tacaactcta acaaatcagc acaaacaaac      60
tcaattacac caataatcaa aattactaac acatctgaca gtgatttaaa tttaaatgac     120
gtaaaagtta gatattatta cacaagtgat ggtacacaag acaaactttt ctggtgtgac     180
catgctggtg cattattagg aaatagctat gttgataaca ctagcaaagt gacagcaaac     240
ttcgttaaag aaacagcaag cccaacatca acctatgata catatgttga atttggattt     300
gcaagcggag cagctactct taaaaaagga caatttataa ctattcaagg aagaataaca     360
aaatcagact ggtcaaacta cactcaaaca aatgactatt catttgatgc aagtagttca     420
acaccagttg taaatccaaa agttacagga tatataggtg gagctaaagt acttggtaca     480
gcaccaggtc cagatgtacc atcttcaata attaatccta cttctgcaac atttgataaa     540
aatgtaacta acaagcaga tgttaaaact actatgactt taaatggtaa cacatttaaa     600
acaattacag atgcaaacgg tacagctcta aatgcaagca ctgattatag tgtttctgga     660
aatgatgtaa caataagcaa agcttattta gcaaaacaat cagtaggaac aactacatta     720
aactttaact ttagtgcagg aaatcctcaa aaattagtaa ttacagtagt tgacacacca     780
gttgaagctg taacagctac aattggaaaa gtacaagtaa atgctggaga acggtagca      840
gtaccagtta acttaacaaa agttccagca gctggtttag caacaattga attaccatta     900
acttttgatt ctgcatcatt agaagtagta tcaataactg ctggagatat cgtattaaat     960
ccatcagtaa acttctcttc tacagtaagt ggaagcacaa taaaattatt attcttagat    1020
gatacattag gaagccaatt aatcactaag gatggagttt ttgcaacaat aacatttaaa    1080
gcaaaagcta taactggaac aactgcaaaa gtaacttcag ttaaattagc tggaacacca    1140
gtagttggtg atgcgcaatt acaagaaaaa ccttgtgcag ttaacccagg aacagtaact    1200
atcaatccaa tcgataatag aatgcaaatt tcagttggaa cagcaacagt aaaagctgga    1260
gaaatagcag cagtgccagt aacattaaca agtgttccat caactggaat agcaactgct    1320
gaagcacaag taagttttga tgcaacatta ttagaagtag catcagtaac tgctggagat    1380
atcgtattaa atccaacagt aaacttctct tatacagtaa acggaaatgt aataaaatta    1440
ttattcctag atgatacatt aggaagccaa ttaattagta aagatggagt ttttgtaaca    1500
ataaacttca agcaaaagc tgtaacaagc acagtaacaa caccagttac agtatcagga    1560
acacctgtat ttgcagatgg tacattagca gaagtacaat ctaaaacagc agcaggtagc    1620
gttacaataa atattggaga tcctata                                        1647
```

ENZYME COMPLEX COMPRISING HEME POLYMERASE AND HEME LIGASE, AND METHOD FOR PRODUCING HEMOZOIN USING SAME

CROSS REFERENCE TO RELATED APPLICATION(S)

This application is a U.S. national stage application of International Application No. PCT/KR2017/014181 filed on Dec. 6, 2017, which claims the benefit of Korean Patent Application No. 10-2016-0164899 filed on Dec. 6, 2016, in the Korean Intellectual Property Office, the entire disclosures of which are incorporated herein by reference for all purposes.

TECHNICAL FIELD

The present invention relates to an enzyme complex comprising heme polymerase and heme ligase, and more particularly to an enzyme complex in which heme polymerase and heme ligase are linked via interaction between a scaffold protein and a dockerin module of cellulase, and to a method of producing hemozoin using the same.

BACKGROUND ART

Bioplastics are plastics made by synthesizing macromolecular polyester in microorganisms such as hydrogen bacteria or nitrogen bacteria. For example, these bioplastics are composed of aliphatic polyester resins produced from starch, sugars, carbohydrates, vegetable oils or fats by a direct fermentation process. These bioplastics are biodegradable because these hard plastics are naturally degraded by degradation enzymes released from microorganisms after the lapse of a certain time after being wasted. These bioplastics have a great advantage in that they are more environmentally sustainable than petrochemical-based plastics due to the use of bio-raw materials and are very environmentally friendly. In particular, in regard to environmental protection and the onset of climate warming, bioplastics are becoming increasingly important not only in the packing sector, but also in the manufacture of long-lasting industrial plastic products.

In the field of studies on useful plastics, many studies have been conducted on functional bioplastics, but studies on the production of conductive bioplastics are still insufficient.

Hemozoin, a by-product of hemoglobin digestion by malaria parasites, is insoluble, and thus depletes iron and intensifies anemia. When a malarial pigment, a component of hemozoin, is deposited, the color of the organs changes to dark brown or black.

Hemozoin is about 1 μm in size, and is present as a crystallized hemoglobin protein which is produced to detoxify the heme moiety generated during the hemoglobin protein metabolism of erythrocytes while malaria parasites are parasitized in the erythrocytes. This hemozoin may be magnetically paramagnetic and optically birefringent.

Previous studies have focused on hemozoin studies in order to utilize the property of hemozoin that responds to magnetic fields, for the purpose of diagnosis of malaria larval survival and malaria (Rebelo, M. et al., Acta. Trop. 123:58,2012; Rebelo, M. et al., Cytometry A. 87:437, 2015; Karl, S. et al., Malaria J. 7:66, 2008).

Accordingly, the present inventors have made extensive efforts to develop a method for producing conductive bioplastics. As a result, the present inventors have produced an enzyme complex of heme polymerase and heme ligase and have found that the use of the enzyme complex makes it possible to efficiently produce a conductive hemozoin polymer, thereby completing the present invention.

DISCLOSURE OF INVENTION

Technical Problem

It is an object of the present invention to provide an enzyme complex that is capable of producing hemozoin from heme.

Another object of the present invention is to provide a method for producing hemozoin, comprising polymerizing heme using the enzyme complex that is capable of polymerizing hemozoin.

Technical Solution

To achieve the above objects, the present invention provides an enzyme complex in which heme polymerase and heme ligase are linked via interaction between a cohesion module of scaffold protein and a dockerin module of cellulase.

The present invention also provides a method for producing the above-described enzyme complex, comprising the steps of: (a) preparing a heme polymerase having a dockerin module bound thereto; (b) preparing a heme ligase having a dockerin module bound thereto; and (c) mixing the heme polymerase and the heme ligase to produce the enzyme complex.

The present invention also provides a method for producing hemozoin, comprising polymerizing heme using the above-described enzyme complex.

BEST MODE FOR CARRYING OUT THE INVENTION

Previous studies on hemozoin have been mostly focused on diagnosis which is performed using the magnetic properties of materials. However, in the present invention, a magnetic hemozoin polymer was produced using enzymes derived from *E. coli*, and it was confirmed that this magnetic hemozoin polymer has the potential to be developed into bioplastic.

In the present invention, in order to develop an enzymatic conversion technology of producing a large amount of hemozoin applicable to conductive bioplastic and to improve the efficiency of conventional heme polymerase, a complex of two different enzymes having the ability to polymerize heme was prepared, thereby increasing the efficiency with which hemozoin is produced by polymerization of heme.

Therefore, in one aspect, the present invention is directed to an enzyme complex in which heme polymerase and heme ligase are linked via interaction between a scaffold protein and a dockerin module of cellulase.

In one example of the present invention, the heme polymerase and heme ligase derived from a *Plasmodium* sp. strain were introduced into an *E. coli* expression vector and expressed, and it was confirmed that the heme-converting enzymes were expressed at high levels from the recombinant strain and easily operated.

In one example of the present invention, a fragment obtained by fusing the dockerin module gene of cellulase to each of the exon 2 portion of *Plasmodium* sp. strain-derived heme polymerase (histidine rich protein 2) gene and heme ligase exon 1-exon 2-exon 3 fusion gene was introduced into an *E. coli* expression vector and expressed. As a result, it was confirmed that a heme polymerase fusion protein having the dockerin module linked thereto and a heme ligase fusion protein having the dockerin module linked thereto were produced.

The heme polymerase fusion protein and the heme ligase fusion protein were linked to each other via the dockerin module with a scaffold protein, thereby producing an enzyme complex.

In the present invention, the dockerin module may be derived from endo-beta-1,4-glucanase-B.

In the present invention, the heme polymerase may be encoded by a nucleotide sequence represented by SEQ ID NO: 3, and the heme ligase is encoded by a nucleotide sequence represented by SEQ ID NO: 28.

In the present invention, in order to improve the efficiency of conventional heme polymerase, an enzyme complex was prepared in which heme polymerase and heme ligase are linked via interaction between a scaffold protein and a dockerin module of cellulase, thereby increasing the efficiency with which hemozoin is produced by polymerization of heme.

Therefore, in another aspect, the present invention is directed to a method for producing the above-described enzyme complex, comprising the steps of: (a) preparing a heme polymerase having a dockerin module bound thereto; (b) preparing a heme ligase having a dockerin module bound thereto; and (c) mixing the heme polymerase and the heme ligase to produce the enzyme complex.

In the present invention, hemozoin was produced from heme using the prepared enzyme complex in which heme polymerase and heme ligase are linked via interaction between a scaffold protein and a dockerin module of cellulase, thereby increasing the efficiency with which hemozoin is produced by polymerization of heme.

Therefore, in still another aspect, the present invention is directed to a method for producing hemozoin, comprising polymerizing heme using an enzyme complex capable of producing hemozoin.

In one example of the present invention, 100 µM heme dissolved in a N,N-dimethylformamide solvent was used as a substrate and the enzyme complex was reacted using 500 mM sodium acetate (pH 5.2) as a reaction buffer at 37° C. for 12 hours. Then, the amount of hemozoin produced by polymerization of heme was measured at a wavelength of 400 nm using an absorbance analyzer. As a result, it was confirmed that the heme polymerization activity was higher when heme polymerase and heme ligase were used in combination than when the polymerase was used alone, and that the polymerization activity was 1.4-fold more increased when the heme polymerase complex was used compared to that heme polymerase and heme ligase were used in combination.

The heme-converting enzyme complex developed according to the present invention can effectively act on the biological conversion of heme to hemozoin, and thus can produce a hemozoin polymer in an economical, cost-effective and efficient manner. This complex is expected to be an invention which is useful for processes. Accordingly, hemozoin converted from heme may be useful as conductive bioplastic, and thus is expected to be a very useful invention for various industrial processes.

As used herein, the term "vector" refers to an expression vector capable of expressing a target protein in suitable host cells and to a genetic construct that includes essential regulatory elements to which a gene insert is operably linked in such a manner as to be expressed.

In general, a plasmid vector is an extrachromosomal cyclic double-stranded DNA and performs various functions in cells. It acts as an inhibitor that kills similar strains or species by producing antibiotic-resistant substances and bacteriocin, and performs biological functions, such as pigment production, compound decomposition and nitrogen fixing. It has a restriction enzyme site so that an exogenous DNA fragment having a length of up to about 10 kb can be inserted therein.

In order to overcome the possibility of inserting only a relatively small DNA fragment, which is a serious disadvantage of a plasmid vector and bacteriophage, cosmid which is an engineered hybrid of a plasmid and phase DNA may be used to clone a larger DNA fragment.

The vector has a cos site which is packaged into a phage particle, and also has a plasmid replication origin that replicates in a bacterial host, and a gene capable of selecting a plasmid. It is packaged into a protein envelope in a test tube, like a bacteriophage vector. However, after an *E. coli* host cell is infected with the packaged DNA, the DNA replicates as a plasmid rather than bacteriophage DNA, and is not lysed. It is 2.5 kb in size, and after it is packaged into a host cell by infection, the cos site has a size of 37 kb to 52 kb. After separation, it contains foreign DNA as an insert. In generally, one having a size of 35 kb to 45 kb may be cloned as a cosmid vector.

In addition, phage, a common type of bacteriophage vector, is derived from a 50-kb double-strand wild-type genome that has single-strand complementary ends of 12 nucleotides that can form base pairs, which are called cohesive termini or cos. Host cells are lysed in a lytic pathway after replication of a new virus and release of a progeny virus. This type of DNA may have 3 kb added to the total size of 52 kb, and may also contain only 5% of the genome. A vector providing a space for foreign DNA is free of nonessential DNA fragments.

A vector related to the present invention includes plasmid vectors (e.g., pSC101, ColEl, pBR322, pUC8/9, pHC79, and pUC19), cosmid vectors, bacteriophage vectors (e.g., gt4B,-Charon, z1 and M13), and viral vectors.

The viral vector includes a vector derived from retrovirus, for example, human immunodeficiency virus (HIV), murine leukemia virus (MLV), leukemia virus (e.g., avian sarcoma and leukosis virus, ASLV), spleen necrosis virus (SNV), Rous sarcoma virus (RSV), mouse mammary tumor virus 8(MMTV), adeno-associated virus (AAV), and herpes simplex virus, but is not limited thereto.

As used herein, the term "operably linked" means that a nucleic acid expression control sequence is functionally linked to a nucleic acid sequence encoding the protein of interest so as to execute general functions. Operable linkage with the recombinant vector can be performed using a gene recombination technique well known in the art, and site-specific DNA cleavage and ligation can be performed using enzymes generally known in the art.

As used herein, the term "regulatory element" means an untranslated nucleic acid sequence that assists in, enhances, or otherwise affects the transcription, translation or expression of a nucleic acid sequence that encodes a protein. The expression vector of the present invention essentially includes a genetic circuit of the present invention as a regulatory element, and may include an expression regulatory element that can affect the expression of a protein, such as, for example, an initiation codon, a termination codon, a polyadenylation signal, an enhancer, or a signal sequence for membrane targeting or secretion.

A polyadenylation signal increases the stability of transcripts or facilitates cytosolic entry. An enhancer sequence is a nucleic acid sequence which is located at various sites in a promoter and increases transcriptional activity compared to the transcriptional activity of the promoter when the enhancer sequence is absent. Signal sequences include, but are not limited to, a PhoA signal sequence, an OmpA signal sequence, etc., when the host is an *Escherichia* sp. strain; an amylase signal sequence, a subtilisin signal sequence, etc., when the host is a *Bacillus* sp. strain; and a mating factor (MF) signal sequence, a SUC2 signal sequence, etc., when the host is yeast.

In addition, when being a replicable expression vector, the vector may include a replication origin, a specific nucleic acid sequence that initiates replication.

The vector according to the present invention may comprise a selection marker. The selection marker is used to select cells transformed with the vector. Here, markers giving selectable phenotypes, such as drug tolerance, auxotrophy, tolerance to cytotoxic agents, or expression of surface proteins, may be used as the selection marker. Since only the cells expressing the selection marker survive in an environment treated with a selective agent, it is possible to select the transformed cells. Representative examples of the selection marker include ura4, leul, his3, etc., which are auxotrophic markers, but the types of markers that may be used in the present invention are not limited by the above examples.

In the present invention, "host cell" means a cell which parasitizes other microorganisms or genes and supply nutrients, and which is transformed with a vector that has various genetic or molecular effects in the host cell. In the competence state of receiving foreign DNA, foreign DNA such as a vector may be inserted into the host cell. When a vector is successfully introduced into the host cell, the genetic character of the vector is provided to the host cell.

Preferably, the host microorganisms of the present invention may be Gram-negative bacteria, which include a *Salmonella* sp. strain, an *Acinebacter* sp. strain, an *Escherichia* sp. strain, a *Pseudomonas* sp. strain, a *Klebsiella* sp, strain, etc. For example, the Gram-negative bacteria include *Salmonella* typhimurium, *Acinebacter* calcoaceticus, *E. coli*, *Pseudomonas* aeruginosa, *Klebsiella* aerogenes, *Acinebacter* baumannii, *Klebsiella* pneumonia, etc., but host cells that can be transformed with the vector of the present invention are not limited thereto.

As a method of introducing a vector into the host cell, a transformation method can be used. As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell. The method of transformation used in the present invention may be any transformation method, and it may be easily performed according to the conventional method used in the art. Examples of the commonly used transformation method may include a $CaCl_2$ precipitation method, the Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation method, a transformation method using polyethylene glycol (PEG), dextran sulfate-, lipofectamine-, and dry/suppression-mediated transformations, etc. The method for transforming the plasmid according to the present invention is not limited to these methods, but any method for transformation commonly used in the art may be used without limitation.

The recombinant vector comprising and the desired gene according to the present invention may be produced using restriction enzymes and polymerase chain reaction (PCR) from a vector which is conventionally used in the art as described above. In addition, the produced vector may be introduced into a host cell by a common transformation technique. In the present invention, the vector was introduced into *E. coli* BL21, and the expression levels of proteins were measured.

In addition, the host cell transformed by the above method may be cultured through a culture method commonly used in the art, if necessary, and the culture medium and period that can be used in the present invention may be selected arbitrarily by a person of ordinary skill in the art, if necessary.

In the present invention, preferably, an *E. coli* strain transformed was cultured in LB (Luria Bertani) medium for 12 hours, and then further cultured for 2 hours to induce production of proteins from recombinant genes. Various media that can be commonly used in the art can be applied to the medium.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1

Amplification of Heme Polymerase and Heme Ligase Genes

To clone enzymes for polymerizing hemozoin, with reference to the nucleotide sequence of the exon 2 portion of a heme polymerase (histidine rich protein 2) gene from the genomic DNA of a *Plasmodium* sp. strain (*Plasmodium falciparum* Welch, ATCC PRA-405D), primers were designed and synthesized such that the restriction enzyme EcoRI recognition sequence was inserted at the 5' end of the forward primer and the restriction enzyme HindIII recognition sequence was inserted at the 5' end of the reverse primer(SEQ ID NOS: 1 and 2). Using the synthesized primers, PCR was performed. As a result, a PCR band containing the exon 2 portion (SEQ ID NO: 3) of the 853-bp heme polymerase gene could be observed.

Primer nucleotide sequences are as follows:

```
SEQ ID NO: 1:
GCGC gaattc g AATAATTCCGCATTTAATAATAACTTGT

SEQ ID NO: 2:
GCGC aagctt ATGGCGTAGGCAATGTGT
```

In addition, with reference to the nucleotide sequence of a heme ligase gene from the genomic DNA of a *Plasmodium* sp. strain (*Plasmodium falciparum* Welch, ATCC PRA-405D), primers were designed so as to remove the intron portion and secure the exons only. For the exon 1 portion of the heme ligase, primers were synthesized such that the restriction enzyme EcoRI was inserted at the 5' end of the forward primer and the N-terminal 10-bp sequence of the exon 2 portion of the heme ligase was inserted at the 5' end of the reverse primer (SEQ ID NOS: 4 and 5).

In addition, for the exon 2 portion of the heme ligase, primers were synthesized such that the C-terminal 10-bp sequence of the exon 1 portion of the heme ligase was inserted at the 5' end of the forward primer, and N-terminal 10-bp sequence of the exon 3 portion of the heme ligase sequence was inserted at the 5' end of the reverse primer (SEQ ID NOS: 6 and 7). Last, for the exon 3 portion of the heme ligase, primers were synthesized such that the C-terminal 10-bp sequence of the exon 2 portion of the heme ligase was inserted at the 5' end of the forward primer, and the restriction enzyme HindIII recognition sequence was inserted at the 5' end of the reverse primer (SEQ ID NOS: 8 and 9). Next, using the synthesized primers, PCR was performed.

As a result, PCR bands containing 216-bp, 204-bp and 195-bp heme ligase exon 1 (SEQ ID NO: 10), exon 2 (SEQ ID NO: 11) and exon 3 (SEQ ID NO: 12) genes were observed.

Primer nucleotide sequences are as follows:

```
SEQ ID NO: 4:
GCGC gaattc g ATGAAAAATAGATTTTATTATAATTTGATAATTAAA
A

SEQ ID NO: 5:
agctgccaac TGTAGGATGATTTAACAGATTAGAA

SEQ ID NO: 6:
tcatcctaca GTTGGCAGCTCGTTAATAC

SEQ ID NO: 7:
acattaacca CGGTTGGTAAGATGAACCA

SEQ ID NO: 8:
ttaccaaccg TGGTTAATGTACAATGAAAAAAGG

SEQ ID NO: 9:
GCGC aagctt AAAAATGATGGGCTTATCTACTATA
```

Example 2

Cloning of Exon 2 Portion of Heme Polymerase (Histidine Rich Protein 2) Gene and Ligation and Cloning of Exon 1, Exon 2 and Exon 3 Genes of Heme Ligase The amplification products of the exon 2 portion of the heme polymerase gene and the heme ligase exon 1, exon 2 and exon 3 genes, obtained in Example 1, were electrophoresed on 0.8% agarose gel, and the DNA fragments on the agarose gel were recovered using a gel extraction kit (GeneAll).

Then, in order to ligate the heme ligase exon 1, exon 2 and exon 3 genes, overlap PCR was performed using the recovered DNA fragments. From the three recovered DNA fragments, primers were designed and synthesized such that the restriction enzyme EcoRI was inserted at the 5' end of the forward primer and the restriction enzyme HindIII recognition sequence was inserted at the 5' end of the reverse primer (SEQ ID NO: 12 and SEQ ID NO: 13). PCR reaction was performed, and as a result, a PCR band containing a 615-bp heme ligase exon gene of the heme ligase exon 1-exon 2-exon 3 fusion gene could be observed.

Primer sequences are as follows:

```
SEQ ID NO: 13:
GCGC gaattc g ATGAAAAATAGATTTTATTATAATTTGATAATTAAA
A

SEQ ID NO: 14:
GCGC aagctt AAAAATGATGGGCTTATCTACTATA
```

Figure 1:
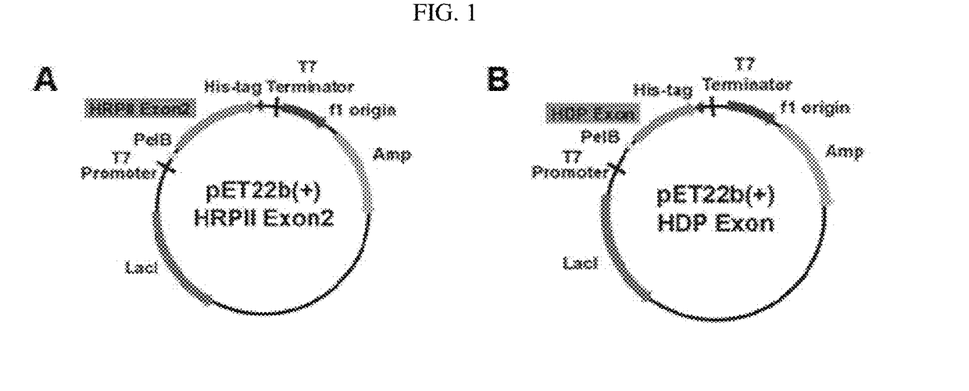
FIG. 1 is a schematic view of the recombinant plasmids pET22(+) HRPII Exon2 (A) and pET22b(+) HDP Exon (B) inserted with HRPII Exon2 and HDP Exon, respectively, in accordance with the present invention.

Thereafter, each of the exon 2 portion of the heme polymerase gene HrpII and the exon gene of the heme ligase gene Hdp was cleaved, and then ligated into the *E. coli* expression vector pET22b(+) which was then transformed into *E. coli* BL21 using EcoRI and HindIII. Next, the ligated recombinant plasmid DNAs were separated from the transformants. The recombinant plasmids were named pET22b (+) HRPII Exon2 and pET22b(+) HDP Exon and are shown in FIG. 1. Also, the *E. coli* transformants were named BL21/HRPII Exon2 and BL21/HDP Exon.

Example 3

Amplification of Heme Polymerase Exon 2 Gene and Heme Ligase Exon 1-Exon 2-Exon 3 Fusion Gene for Fusion to Dockerin Module of Cellulase For formation of a heme polymerase complex, fusion of the dockerin module gene of cellulase to the exon 2 gene of the heme polymerase obtained in Example 1 and the heme ligase exon 1-exon 2-exon 3 fusion gene was performed.

For the fusion of the dockerin module gene of cellulase to the exon 2 gene of heme polymerase, with reference to the nucleotide sequence of the heme polymerase exon 2 gene obtained in Example 1, primers were synthesized such that the restriction enzyme XbaI was be inserted at the 5' end of the forward primer and the N-terminal 10-bp sequence of the dockerin module of endo-beta-1,4-glucanase-B gene was inserted at the 5' end of the reverse primer (SEQ ID NO: 15 and SEQ ID NO: 16).

Next, using the synthesized primers, PCR was performed. As a result, a 875-bp PCR band containing the heme polymerase exon 2 gene derived from the *Plasmodium* sp. strain could be observed.

In addition, in order to clone the dockerin module gene of cellulase for formation of a heme polymerase complex of the heme polymerase exon 2 gene, with reference to the nucleotide sequence of the dockerin module of the endo-beta-1,4-glucanase-B gene from the genomic DNA of *Clostridium cellulovorans*, primers were designed and synthesized such that the C-terminal 10-bp sequence of the heme polymerase exon 2 gene derived from the *Plasmodium* sp. strain was inserted at the 5' end of the forward primer, and the restriction enzyme PstI recognition sequence was inserted at the 5' end of the reverse primer (SEQ ID NO: 17 and SEQ ID NO: 18). Next, using the synthesized primers, PCR was performed.

As a result, a 222-bp PCR band containing a dockerin module gene of the endo-beta-1,4-glucanase-B gene could be observed.

Primer nucleotide sequences are as follows:

```
SEQ ID NO: 15:
GCGC tctaga tttaagaaggagatatacat ATG

AATAATTCCGCATTTA

SEQ ID NO: 16:
cagcggatcc ATGGCGTAGGCAATGTGT

SEQ ID NO: 17:
cctacgccat GGATCCGCTGGCTCC

SEQ ID NO: 18:
ATAT ctgcag tca gtggtggtggtggtggtg

TAAAAGCATTTTTTTAAG
```

For fusion of the dockerin module gene of cellulase to the heme ligase exon 1-exon 2-exon 3 gene, with reference to the nucleotide sequence of the exon 1-exon 2-exon 3 gene obtained by ligation of heme ligase exon 1, exon 2, and exon 3 genes in Example 1, primers were synthesized such that the restriction enzyme XbaI was inserted at the 5' end of the forward primer, and the N-terminal 10-bp sequence of the dockerin module of the endo-beta-1,4-glucanase-B gene was inserted at the 5' end of the reverse primer (SEQ ID NO: 19 and SEQ ID NO: 20).

Next, using the synthesized primers, PCR was performed. As a result, a 641-bp PCR band containing the heme ligase exon 1-exon 2-exon 3 gene derived from the *Plasmodium* sp. strain could be observed.

In addition, with reference to the nucleotide sequence ((SEQ ID NO: 23) of the dockerin module of the endo-beta-1,4-glucanase-B gene from the genomic DNA of *Clostridium cellulovorans*, primers were designed and synthesized such that the C-terminal 10-bp sequence of the heme ligase exon 1-exon 2-exon 3 fusion gene derived from the *Plasmodium* sp. strain was inserted at the 5' end of the forward primer, and the restriction enzyme PstI recognition sequence was inserted at the 5' end of the reverse primer ((SEQ ID NO: 21 and (SEQ ID NO: 22).

Using the synthesized primers, PCR was performed. As a result, a 222-bp PCR band containing a dockerin module gene of the endo-beta-1,4-glucanase-B gene could be observed.

Primer nucleotide sequences are as follows:

```
SEQ ID NO: 19:
GCGC tctaga tttaagaaggagatatacat

ATGAAAAATAGATTTTATT

SEQ ID NO: 20:
cagcggatcc AAAAATGATGGGCTTATCTACTATAT

SEQ ID NO: 21:
catcattttt GGATCCGCTGGCTCCG

SEQ ID NO: 22:
ATAT ctgcag tca gtggtggtggtggtggtg

TAAAAGCATTTTTTTAAG

Dockerin module sequence (SEQ ID NO: 23):
gatgttaacaaagatggaaaggtaaatgctatcgattatgcagtgcttaa atcaattcttttaggtacaaatactaacgttgatttatcagtatcagaca tgaataaggatggtaaagtaaatgctttggatttagctgttcttaaaaaa atgcttta
```

Example 4

Ligation and Cloning of Dockerin Module Gene of Cellulase, Heme Polymerase Exon 2 Gene, and Heme Ligase Exon 1-Exon 2-Exon 3 Gene The amplification products of the heme polymerase exon 2 gene, the heme ligase exon 1-exon 2-exon 3 gene, and the dockerin module gene of cellulase obtained in Example 3, were electrophoresed on 0.8% agarose gel, and the DNA fragments on the agarose gel were recovered using a gel extraction kit (GeneAll).

Then, using the recovered DNA fragments, overlap PCR reaction was performed to ligate the dockerin module gene of cellulase with the heme polymerase exon 2 gene and the heme ligase exon 1-exon 2-exon 3 gene, respectively. From the two recovered DNA fragments, primers were designed and synthesized such that the restriction enzyme XbaI was inserted at the 5' end of the forward primer and the restriction enzyme Pst I recognition sequence was inserted at the 5' end of the reverse primer (SEQ ID NO: 24 and SEQ ID NO: 25).

PCR reaction was performed, and as a result, a 1097-bp PCR band containing the heme polymerase exon 2 gene linked to the dockerin module of cellulase and a 863-bp PCR band containing the heme ligase exon 1-exon 2-exon 3 gene linked to the dockerin module of cellulase (SEQ ID NO: 28) were obtained.

Primer nucleotide sequences are as follows:

SEQ ID NO: 24:
GCGC tctaga tttaagaaggagatatacat ATG

AATAATTCCGCATTTA

SEQ ID NO: 25:
ATAT ctgcag tca gtggtggtggtggtggtg

TAAAAGCATTTTTTAAG

SEQ ID NO: 26:
GCGC tctaga tttaagaaggagatatacat

ATGAAAAATAGATTTATT

SEQ ID NO: 27:
ATAT ctgcag tca gtggtggtggtggtggtg

TAAAAGCATTTTTTAAG

Figure 2:
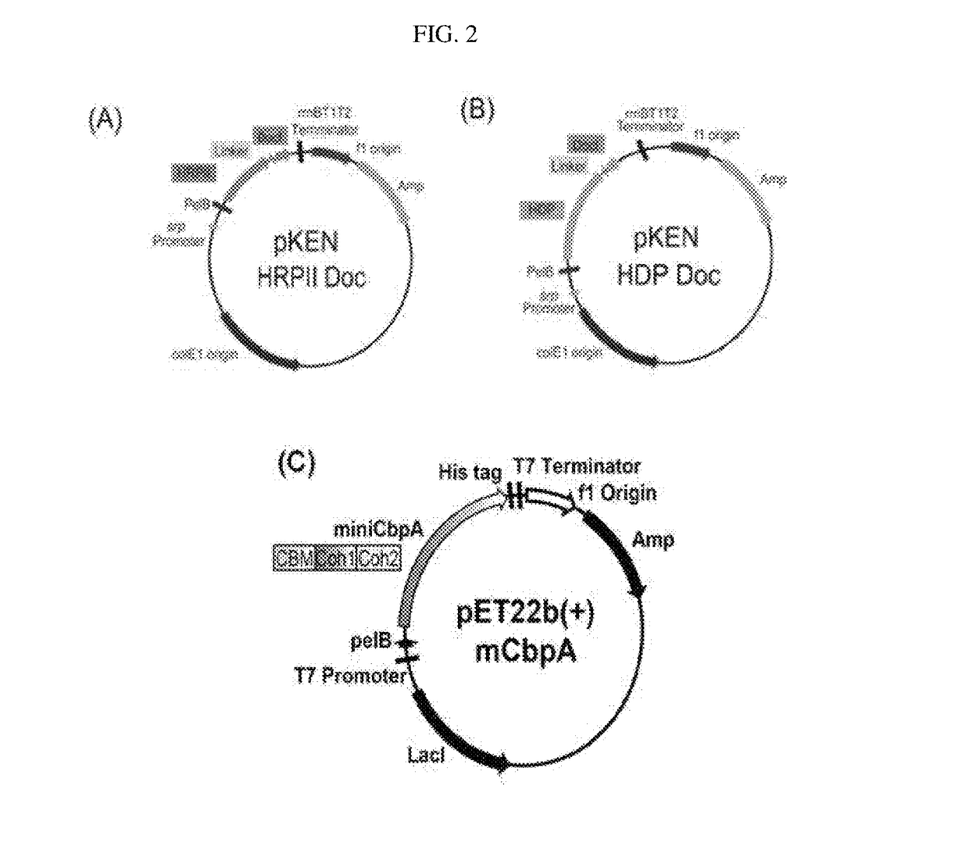
FIG. 2 shows schematic views of the recombinant plasmids pKEN HRPII-Doc (A) inserted with heme polymerase Exon2 gene HRPII-Doc fused with the dockerin module gene of cellulase, the recombinant plasmids pKEN HDP-Doc (B) inserted with the heme ligase exon 1-exon 2-exon 3 gene HDP-Doc fused with the dockerin module gene of cellulase, and the recombinant plasmids pET22b-mCbpA (C) inserted with the mini scaffold protein gene mCbpA having a cohesin module that binds to the dockerin module to form an enzyme complex, in accordance with the present invention.

Thereafter, each of the chimeric heme polymerase gene HRPII-Doc and the chimeric heme ligase gene HDP-Doc was cleaved, and then ligated into the *E. coli* expression vector pKEN which was then transformed into *E. coli* BL21 using Xba I and Pstl. Next, the ligated recombinant plasmid DNAs was separated from the transformants. The recombinant plasmids were named pKEN-HRPII-Doc and pKEN-HDP-Doc and are shown in FIG. 2. Also, the *E. coli* transformants were named BL21/HRPII-Doc and BL21/HDP-Doc.

In addition, in order to clone a mini-cellulose-binding protein A having a cellulose binding module (CBM) and two cohesin modules among cellulose-binding protein A which is a primary scaffolding subunit derived from *Clostridium cellulovorans*, with reference to the nucleotide sequence (GenBank: M73817.1), primers were synthesized such that the restriction enzyme BamHI recognition sequence (ggatcc) was inserted at the 5' end of the forward primer (SEQ ID NO: 29) and the restriction enzyme XhoI recognition sequence (ctcgag) was inserted at the 5' end of the reverse primer (SEQ ID NO: 30). As a result, a 1659-bp PCR band containing a mCbpA gene (SEQ ID NO: 31), a portion of the cellulose-binding protein-A gene derived from *Clostridium cellulovorans*, could be observed.

SEQ ID NO: 29:
ggatccgcagcgacatcatcaa

SEQ ID NO: 30:
GCGCctcgaggctataggatctccaatatttat

Next, the mini-cellulose-binding protein-A mCbpA gene was cleaved, and then ligated into the *E. coli* expression vector pET22b(+) using BamHI and XhoI, after which the vector was transformed into *E. coli* BL21. Then, the ligated recombinant plasmid DNA was separated from the transformant. The recombinant vector was named pET22b-mCbpA and is shown in FIG. 2. In addition, the *E. coli* transformant was named BL21/mCbpA.

Example 5

Expression of Heme Polymerase and Heme Ligase Proteins in *E. coli* Transformant In order to examine the expression of enzyme proteins in the transformants obtained in Example 2 and 4, His-tag purification and SDS-PAGE were performed.

The *E. coli* transformant was treated with IPTG to induce the expression of heme polymerase and heme ligase proteins, and then shake-cultured at 16° C. for 12 hours and centrifuged to collect the cells. Then, the cells were disrupted using ultrasonic waves and centrifuged, and the supernatant was concentrated (Millipore, amicon 10kDa cut off) to obtain the corresponding proteins which were then loaded onto SDS-PAGE.

Next, Western blot analysis was performed using a His-tag attached to the C-terminal end of each protein.

Figure 3:
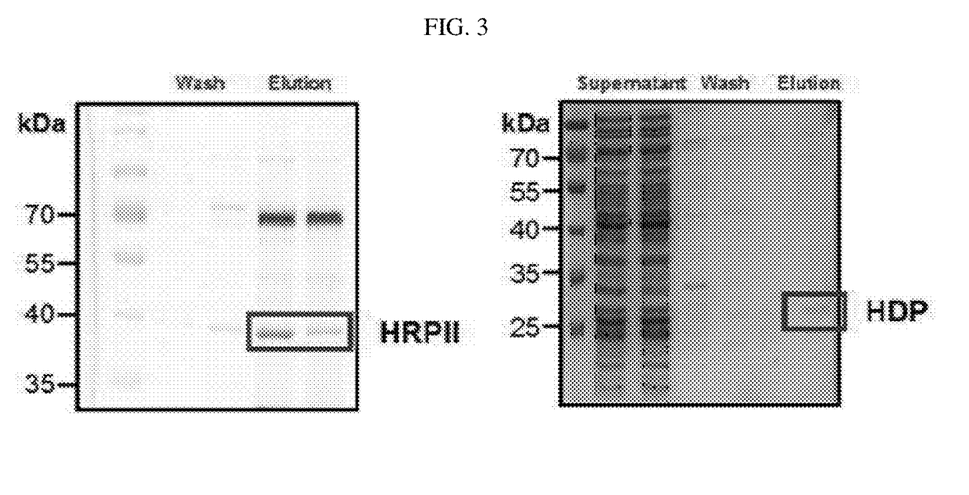
FIG. 3 shows the results of SDS-PAGE analysis after His-tag purification of proteins performed to analyze the expression of proteins in *E. coli* strain inserted with the recombinant plasmids pET22(+) HRPII Exon2 and pET22b (+) HDP Exon, in accordance with the present invention.
Figure 4:
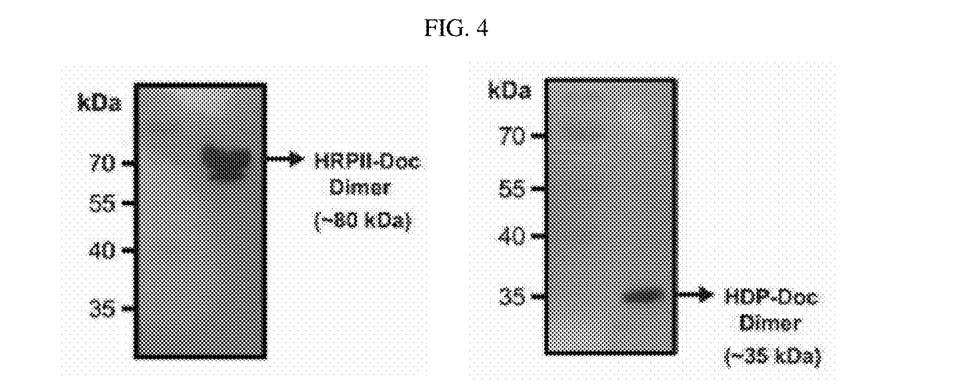
FIG. 4 shows the results of Western blot analysis performed to analyze the expression of proteins in an *E. coli* strain inserted with the recombinant plasmids pKEN HRPII-Doc and pKEN HDP-Doc in accordance with the present invention.

As a result, it could be seen that the protein bands appeared at the same positions as the expected protein sizes. The results are shown in FIGS. 3 and 4, respectively.

In order to confirm scaffold protein/enzyme complex formation caused by a combination of heme polymerase and heme ligase, a purification experiment based on the carbohydrate binding module (CBM) of the scaffold protein was performed using cellulose as resin.

Expression of protein in the BL21/mCbpA recombinant strain was induced under the condition that the mCbpA protein was secreted into culture medium. The strain was inoculated into LB medium and cultured at 37° C. for 24 hours and cultured in IPTG-containing LB liquid medium for 5 hours more, and the supernatant was concentrated (Millipore, amicon 10kDa cut off) to obtain mCbpA, a mini-cellulose-binding protein A. For protein purification based on the interaction between a cellulose binding module (CBM) and cellulose, a reaction was performed in the presence of cellulose (Sigmacell Type 50, SIGMA) at room temperature for 1 hour. After the reaction, the reaction solution was rinsed three times with 0.02 M Tris buffer (pH 8.0) containing 1 M sodium chloride, and then eluted with 0.05 M Tris buffer (pH 12.5). The enzyme protein was electrophoresed by SDS-PAGE on 10% poly-acrylamide gel.

Figure 5:
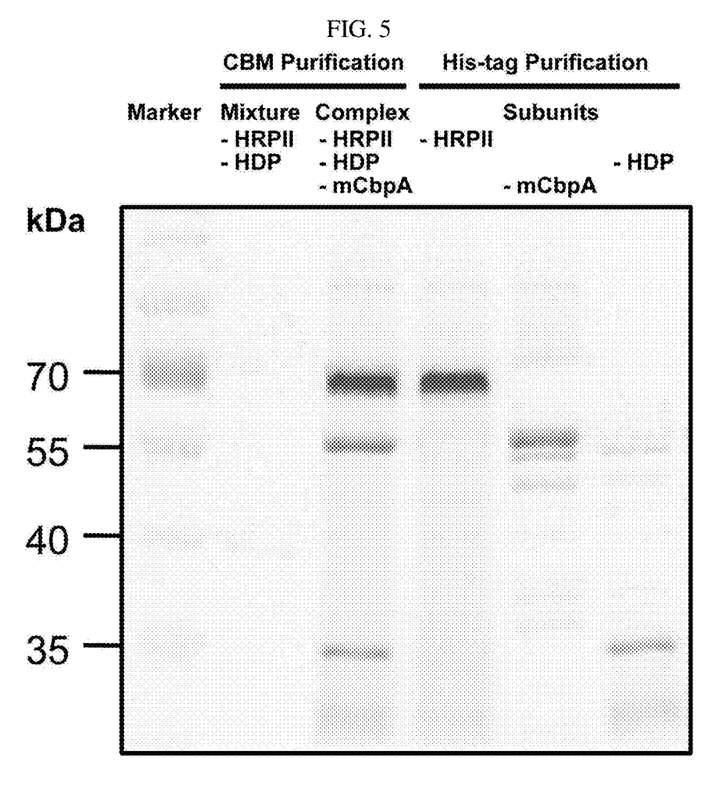
FIG. 5 shows the results of SDS-PAGE analysis performed to confirm the formation of an enzyme complex according to the present invention. Purification with cellulose bar carbohydrate binding module in scaffold protein indicated the formation of the enzyme complex, and His-tag purification indicated the presence of proteins corresponding to the respective subunits.

Only when heme polymerase and heme ligase bind to the scaffold protein to form an enzyme complex, purification with cellulose was possible. To confirm this fact, SDS-PAGE analysis was performed, and it was confirmed that proteins corresponding to the respective subunits purified with the His-tag were present. The results are shown in FIG. 5.

Example 6

Combination of Heme Polymerase and Heme Ligase and Analysis of Activity

In order to confirm the polymerization activity of a combination of heme polymerase and heme ligase, the analysis of heme polymerization activity was performed using heme as a substrate for when heme polymerase and heme ligase were each used alone; when heme polymerase and heme ligase were used in combination; and a complex of heme polymerase and heme ligase was used.

In the method of analyzing the activity, 100 μM heme dissolved in a N,N-dimethylformamide solvent was used as a substrate and each enzyme(s) were subjected to a polymerization reaction using 500 mM sodium acetate (pH 5.2) as a reaction buffer at 37° C. for 12 hours. Then, the amount of hemozoin polymer produced was measured using an absorbance analyzer at a wavelength of 400 nm.

Figure 6:
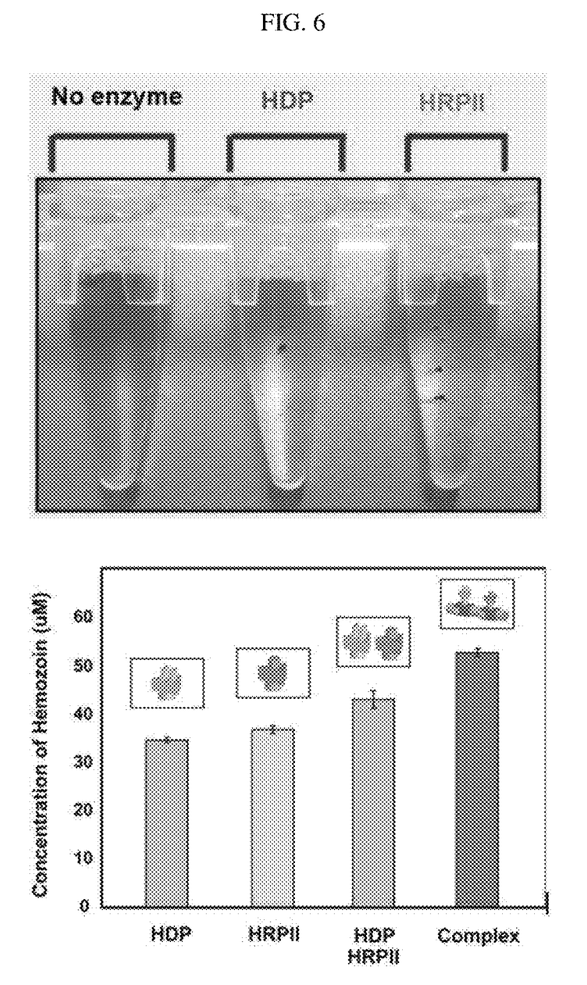
FIG. 6 shows the results of analyzing the heme polymerization activity of a complex obtained by assembling *Plasmodium* sp. strain-derived heme polymerase HRPII-Doc and chimeric heme ligase HDP-Doc proteins with each other, each of which has bound thereto the dockerin module of endo-beta-1,4-glucanase-B gene. The analysis was performed using heme as a substrate and the heme polymerase complex showed increased activity.

As a result of the method performed as described above, it was confirmed that the activity was higher when the polymerization was performed using the combination of heme polymerase and heme ligase than when the polymerase was used alone, and that the activity was 1.4-fold more increased when the heme polymerase complex was used than the activity when the combination was used. The results are shown in FIG. 6.

INDUSTRIAL APPLICABILITY

The enzyme complex according to the present invention can polymerize heme with higher efficiency than conventional enzymes, and thus can more efficiently produce hemozoin, a conductive biopolymer. Therefore, the inventive enzyme complex is expected to be used with advantages in environmental and economic terms.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An enzyme complex comprising a heme polymerase, a heme ligase, and a scaffold protein, wherein the heme polymerase comprises a first dockerin module of a first cellulase, and the heme ligase comprise a second dockerin module of a second cellulase, wherein the scaffold protein comprises a cohesin module, wherein the heme polymerase and the heme ligase are linked via a protein-protein interaction between the cohesin module, the first dockerin module, and the second dockerin module, and wherein the heme polymerase is encoded by the nucleotide sequence set forth in SEQ ID NO: 3 and the heme ligase is encoded by the nucleotide sequence set forth in SEQ ID NO: 28.

2. The enzyme complex of claim 1, wherein the dockerin module is obtained from endo-beta-1,4-glucanase-B.

3. A method for producing the enzyme complex of claim 1, comprising the steps of:
   (a) preparing a heme polymerase having a first dockerin module of a first celluase bound thereto;
   (b) preparing a heme ligase having a second dockerin module of a second cellulase bound thereto;
   (c) preparing a scaffold protein comprising a cohesin module; and
   (d) mixing the heme polymerase and the heme ligase with the scaffold protein such that the heme polymerase and the heme ligase are linked via a protein-protein interaction between the cohesin module, the first dockerin module, and the second dockerin module.

* * * * *